United States Patent [19]

Tedder

[11] Patent Number: 4,517,298

[45] Date of Patent: May 14, 1985

[54] PROCESS FOR PRODUCING FUEL GRADE ETHANOL BY CONTINUOUS FERMENTATION, SOLVENT EXTRACTION AND ALCOHOL SEPARATION

[75] Inventor: Daniel W. Tedder, Marietta, Ga.

[73] Assignee: Georgia Tech Research Corporation, Atlanta, Ga.

[21] Appl. No.: 534,262

[22] Filed: Sep. 21, 1983

Related U.S. Application Data

[63] Continuation of Ser. No. 265,328, May 8, 1981, abandoned.

[51] Int. Cl.$^3$ ............ C12P 7/16; C12P 7/06; C10L 1/02
[52] U.S. Cl. ................... 435/160; 435/161; 435/162; 435/165; 435/813; 44/53; 44/56
[58] Field of Search ................ 435/161–165, 435/813, 160; 44/53, 56

[56] References Cited

U.S. PATENT DOCUMENTS

| | | | |
|---|---|---|---|
| 4,094,742 | 6/1978 | Bellamy | 435/165 X |
| 4,242,455 | 12/1980 | Muller et al. | 435/813 X |
| 4,251,231 | 2/1981 | Baird | 568/918 X |
| 4,306,884 | 12/1981 | Roth | 568/918 X |

FOREIGN PATENT DOCUMENTS 2013716A 8/1979 United Kingdom ............ 435/162

Primary Examiner—Robert Yoncoskie
Attorney, Agent, or Firm—Newton, Hopkins & Ormsby

[57] ABSTRACT

Alcohol substantially free of water is prepared by continuously fermenting a fermentable biomass feedstock in a fermentation unit, thereby forming an aqueous fermentation liquor containing alcohol and microorganisms. Continuously extracting a portion of alcohol from said fermentation liquor with an organic solvent system containing an extractant for said alcohol, thereby forming an alcohol-organic solvent extract phase and an aqueous raffinate. Said alcohol is separated from said alcohol-organic solvent phase. A raffinate comprising microorganisms and unextracted alcohol is returned to the fermentation unit.

14 Claims, 1 Drawing Figure

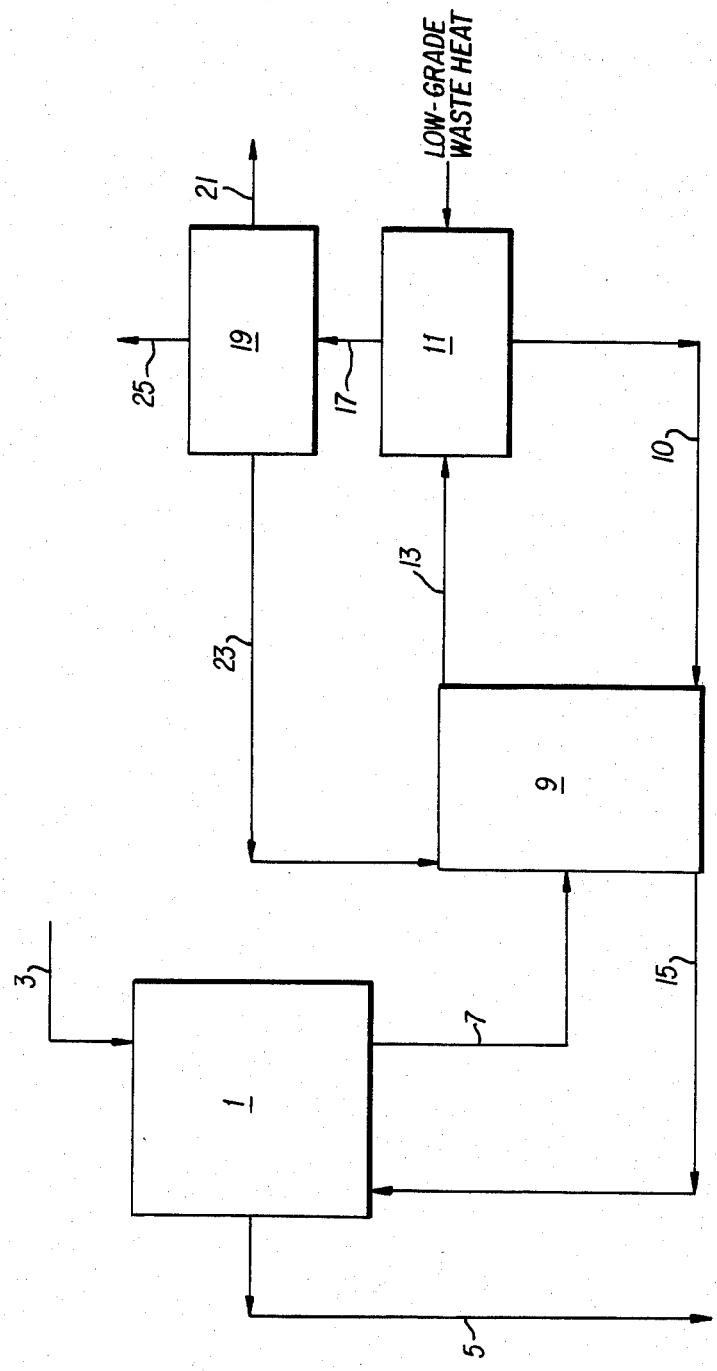

PROCESS FOR PRODUCING FUEL GRADE ETHANOL BY CONTINUOUS FERMENTATION, SOLVENT EXTRACTION AND ALCOHOL SEPARATION

This application is a continuation of application Ser. No. 265,328, filed 5/8/81, now abandoned.

BACKGROUND OF THE INVENTION

1. Field of the Invention

The present invention relates to a method for preparing fuel grade alcohol.

2. Description of the Prior Art

Ethanol as well as other alcohols is commonly prepared by fermentation of sugars or other biological feedstocks. In the fermentation process, the fermentable materials including yeast microorganisms are added to a large tank where fermentation is accomplished in a batch process. During fermentation the yeast cells or other microbes used consume the biomass feedstock in the tank and convert the feedstock to alcohol as they grow. The initial rate of fermentation is low, but then increases to a maximum rate which decreases again as the alcohol content in the fermentation medium increases. In fact, in the case of wine production, the relatively high alcohol content in the final product may be sufficient to actually kill the fermenting microorganisms.

After the fermentation has reached the desired stage of completion, the fermentation liquors are drained from the tank. Thereafter, if fuel grade ethanol is to be recovered from the ferment, the fermentation liquors are clarified in a beer still and then fractionated to produce an ethanol-water azeotrope.

The conventional process for producing fuel grade ethanol has several drawbacks. One of the disadvantages is that the fermentation step is operated bathwise which means that the average rate of conversion of fermentable material is lower than would be the case if the fermentation was conducted continuously. Consequently, the quantities of fermentable feedstocks must be maintained at high levels at the processing plant in order to maintain the desired production rate. Secondly, the distillation process for the recovery of ethanol is highly energy intensive. An analysis of the conventional alcohol distillation process shows that the total amount of energy required to obtain absolute ethanol from the fermentation liquor is about 60% of the theoretical heating value of the ethanol product. This is a significant disadvantage for the large scale production of essentially water free ethanol for use as an ingredient in the production of gasoline - alcohol mixtures (commonly known as gasahol) which are to be used as motor fuels. If, in fact, ethanol is to find acceptable commercial utility as a motor fuel ingredient, the energy required to produce the substantially water free ethanol must be less than the energy that can be recovered from the combustion of the ethanol as a fuel. Moreover, the conventional distillation and recovery process is complicated since it requires three distinct processing steps which are the (1) beer still, (2) the fractionator and (3) the azeotropic distillation with benzene. A need, therefore, continues to exist for a method by which substantially water free alcohol, particularly ethanol, can be obtained using substantially less energy for the recovery of alcohol in comparison to conventional alcohol recovery procedures.

SUMMARY OF THE INVENTION

Accordingly, one object of the present invention is to provide a technique by which substantially water free alcohol can be produced under conditions which reduce energy consumption to about 20% or less of that required by conventional methods.

Another object of the present invention is to simplify recovery methodology for substantially water free alcohol from aqueous fermentation liquors.

Still another object of the present invention is to provide a method of recovering substantially water free alcohol from aqueous fermentation liquors which utilize the low grade heat generated by the fermentation process.

Yet another object of the present invention is to provide a continuous method of fermenting biomass feedstock by maintaining a given level of alcohol concentration in the fermentation medium.

Briefly, these objects and other objects of the present invention as hereinafter will become more readily apparent can be attained by a method of producing alcohol substantially free of water by continuously fermenting a fermentable biomass feedstock in a fermentation unit thereby forming an aqueous fermentation liquor containing alcohol, continuously withdrawing a portion of the alcohol containing liquor, contacting the withdrawn liquor with an organic solvent system containing an extractant for the alcohol thereby forming an alcohol-solvent extract phase and an aqueous raffinate, and separating the alcohol from the alcoholsolvent phase.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawing, wherein:

FIG. 1 is a flow diagram of the continuous fermentation-distillation procedure of the present invention.

DETAILED DESCRIPTION OF THE PREFERRED EMBODIMENTS

The present invention involves a method of producing alcohol which is at least substantially free of water and preferably completely free of water. The term alcohol as used in the present invention embraces the common simple aliphatic alcohols, most particularly ethanol. Alcohol substantially free of water is known as fuel grade alcohol, which is generally 96+% alcohol.

In the first step of the present process, a biomass feedstock is continuously fermented in an aqueous medium in a conventional fermentation unit thereby forming an aqueous liquor pregnant with alcohol. During fermentation biomass feedstock is continuously added to the fermentation unit along with the necessary fermenting microorganisms, while aqueous fermentation liquor is continuously withdrawn for further processing and sludge waste is withdrawn for processing. An interesting feature of the continuous fermentation step of the present invention is that by continuous withdrawal of fermentation liquor from the fermentation unit and extraction of alcohol from the liquor and by recycle of aqueous raffinate from the extraction step to the fermentation unit and addition of feedstock to the fermentation unit, the concentration level of alcohol in the fermentation unit can be maintained at a constant desired level. Moreover, the temperature of the fermentation liquor in the fermentation unit can be maintained at a given desired level optimum for fermentation, which is a slightly exothermic process, by the recycle of cooled aqueous raffinate from the extraction step. Generally, the temperature is maintained at a level of 25° C. to 35° C., although when thermophilic bacteria are used the temperature can range as high as 75° to 95° C. Moreover, the fermentation step of the present invention can be conducted under known, conventional fermentation conditions.

Suitable biomass feedstocks which can be employed in the fermentation step of the present process include sugar based materials such as molasses, sugar beets, sugar cane and the like. Other biomass feedstocks include grains such as corn, wheat, barley, and the like and cellulosic material such as wood chips and the like.

The fermenting microorganisms which ferment the biomass feedstock can be any known microorganism used in fermentation processes to produce alcohols such as various species of yeast which include Candida, Saccharomyces and the like as well as thermophilic bacteria.

For a clearer understanding of the process of the present invention including the continuous fermentation step, reference is made to the figure which shows biomass feedstock and microorganisms entering fermentation unit 1 by line 3. Fermentation unit 1 besides having the capacity to conduct fermentation also possesses the means of decanting sludge wastes which develop during processing from the unit. Sludge wastes are removed from unit 1 through line 5. The fermentation liquid is then further treated and clarified in the likes of a beer still or it is centrifuged, decanted or filtered or pressed. Dilute alcohol containing fermentation liquor is withdrawn from unit 1 through line 7 to solvent extraction unit 9. The solvent system for the extraction step 9 as a recycled material from alcohol-solvent separation unit 11 continuously reenters extraction unit 9 via line 10. On the other hand, the organic solvent-alcohol phase which forms in extraction unit 9 and which is substantially free of water is discharged from unit 9 via line 13 to alcohol-solvent separation unit 11. Aqueous raffinate which separates from the organic solvent-alcohol phase in unit 9 is transferred to fermentation unit 1 via line 15.

The continuous fermentation unit 1 in combination with the continuous extraction unit 9 provides an important advantage in that the combined apparatus are more efficient together than when operated separately. Because alcohol can be continuously removed from the alcohol under very mild conditions, the yeast or other fermenting microbes are not destroyed in the alcohol extraction process. Moreover, the continuous removal of fermentation products permits fermentation to occur under optimum conditions thereby minimizing fermenting unit capacity. The recycling of aqueous raffinate from unit 9 to unit 1 is an advantageous feature in that the raffinate is not treated as a waste material which normally would be discarded. If the raffinate were to be discarded, the alcohol would have to be removed with a high degree of proficiency. This would require an extraction cascade having more extraction stages than are required in the present case where the extraction efficiency must not be nearly as extensive. In fact, in the present process the extraction efficiency of unit 9 can be operated at a relatively low level of alcohol removal such as on the order of about 50% alcohol removal per pass. Because the required solvent/aqueous alcohol ratio under the less demanding extraction conditions of the present process is reduced, the alcohol recovery process is more efficient.

In the alcohol-solvent separation unit 11, alcohol is separated from the components of the organic solvent system, the relative ease of which separation is determined by the solvent chosen. Preferably, a high molecular weight solvent is selected so that the vapor pressure of the solvent is must less than the vapor pressure of the dissolved alcohol. The low grade of heat produced during fermentation is sufficient to distill the solvent phase-alcohol mixture under vacuum conditions. Suitable types of conventional extraction units which can be employed in the present invention include pulse columns, banks of mixer-settlers and high speed centrifugal contactors. Alcohol at least substantially free of water is discharged from unit 11 via line 17 to condensation unit 19 where the alcohol is condensed. Most of the alcohol product is withdrawn for use from the condenser through line 21, while that amount of essentially dry alcohol needed to adequately dry the organic solvent system ethanol phase at the top of unit 9 is recycled to the unit through line 23. Noncondensible off-gases generated in the system are discharged from the system via line 25.

An important aspect of the alcohol separation and recovery process of the present invention pertains to the extracting organic solvent system. The organic extractant component of the solvent system should be one which readily complexes with alcohol and at the same time is one in which water is essentially immiscible. The solvent should also have a substantially lesser vapor pressure than that of the alcohol. Under these limitations, the relative volatility difference between the alcohol and solvent will be large.

The ability of an organic extractant to efficiently separate two similar molecules such as water and an alcohol depends on a delicate balance between several structural features. Factors such as hydrogen bonding capabilities, charge distribution, steric environment of coordinating centers and hydrophobic-hydrophilic balance are important considerations in recovering fuel grade alcohol efficiently. Clearly, the presence of a zwitter ionic structure in the extractant molecule (or semi polar bond) in which negative charge in the molecule protrudes into the organic solvent medium and the positive charge is embedded in a hydropohobic environment are important structural features. This arrangement should heighten the hydrogen bonding capabilities of the extractant and diminish the extent of aggregation of extractant in the hydrocarbon solvent. In order to decrease the degree of water complexation structural features should be incorporated in the extractant that prevent the two extractant molecules from becoming proximate to one another to form a bridged structure with bridging water molecules. Secondary hydrogen bonding sites such as -O-R components should be either eliminated or sterically encumbered so as to prevent additional interactions with water molecules. Finally, enough hydrophobic hydrocarbon framework should be incorporated into the extractant molecules to prevent any significant solubility in the aqueous alcohol phase of the extraction zone. These considerations and restrictions suggest the following type of compounds which include symmetric and unsymmetric alkyl and aryl phosphates, phosphonates, phosphine oxides, sulfoxides, sulfones, amine oxides and quaternary ammonium and phosphonium salts of sterically hindered carboxylic acids possessing structural features which facilitate alcohol complexation.

Suitable examples of organic extractant compounds for use in the organic solvent system include di-2-ethyl hexyl-2-ethyl hexyl phosphonate, trineopentylphosphate, cyclohexyl di-t-butylphosphate, tri-2,6-dimethylphenylphosphate, triphenylphosphine oxide, di-neopentyl sulfoxide, di-neopentylsulfone, tri-isopropylamine oxide, tetra-n-butylammonium-2, 6-di-t-butylbenzoate, and the like.

In the formulation of a suitable solvent system for the extraction of alcohol from an aqueous alcohol solution, a hydrophobic solvent which is completely miscible with the organic extractant molecule should be employed. Suitable hydrophobic solvents include aliphatic hydrocarbons such as dodecane, kerosene, gasoline, disopropylbenzene and the like.

The scope of the organic solvent system also includes extractants which are capable of hydrogen bonding with water or alcohol. Suitable organic extractants capable of hydrogen bonding include alkyl and aromatic alcohols, carboxylic acids and ethers. Among the alcohols, the high boiling alcohols, i.e., those containing long carbon atom chains of about ten or more, are preferred. In fact, the high boiling alcohols as solvent systems within themselves can be used without a hydrophobic solvent component. Other alcohols include mixed isomers of isodecanol, 2-ethyl hexanol, 2-methyl-2-pentanol, 4-heptanol, 3-ethyl-3-pentanol and the like, as well as diols and triols. The mixed isomers of tridecanol are especially preferred as an extractant.

The organic solvent alcohol phase discharged from the extraction zone 9 is processed in separation zone 11 where the alcohol is separated from the solvent system by conventional distillation or evaporation methodology. Suitable separation techniques include vacuum distillation, solar distillation, falling-film evaporation and carrier gas stripping. The preferred separation technique is vacuum distillation or flash evaporation operated at a reduced pressure of 1 to 500 mm Hg where waste heat from the exothermic fermentation step can be utilized to facilitate distillation. The alcohol vapor discharged from the distillation step can be condensed by standard condenser apparatus. The alcohol product obtained from the present process is substantially free of water and is suitable for use as a motor fuel or motor fuel additive.

The following table shows the estimated energy sinks in a conceptual fuel-grade ethanol recovery process using solvent extraction, vacuum stripping and barometric condensation of the ethanol product.

| EQUIPMENT ITEM | BRAKE HORSE-POWER | ENERGY CONSUMED (% OF ETOH HV)[a] |
|---|---|---|
| Solvent Extraction Mixers (16 required) | 42[b] | 0.11[b] |
| Solvent circulation | 8 | 0.02 |
| Wiped Film Evaporator Mixed | 25 | 0.07 |
| Cold Ethanol Recycle | 63 | 0.17 |
| Ammonia Refrigeration | 3120[c] | 8.41 |
| Cooling Water Recycle | 20 | 0.05 |
| TOTALS | 3341 | 9.00 |

[a]Percentage of the ethanol product heating value (% of EtOH HV) when it is used as a fuel. A 33% efficiency has been assumed in producing electricity.
[b]This is the total for the cascade.
[c]The reference cycle evaporates at −30° F. and condenses at 120° F. to facilitate heat transfer. The energy consumed is 3.2 BHP/ton of refrigeration.

The total energy consumption appears very favorable compared to conventional distillation. This analysis suggests that the energy consumption in drying the product to 96+% ethanol may be reduced from about 61.5% to 9% of the product heating value.

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. A continuous method of preparing alcohol, comprising:
   continuously fermenting with fermentation microorganisms a fermentable biomass feedstock in water in a fermentation unit, thereby forming an aqueous fermentation liquor containing alcohol;
   withdrawing a sludge waste and fermentation liquor comprising microorganisms and alcohol obtained during the processing of the biomass in the processing unit;
   supplying additional feedstock and microorganisms to said fermentation unit;
   continuously extracting a low-level alcohol from said fermentation liquor with a chemically stable organic solvent system containing an extractant for said alcohol and a hydrocarbon solvent for said extractant, said hydrocarbon solvent having ten or more carbons in its atom, thereby forming an alcohol-organic solvent extract phase and an aqueous raffinate;
   separating said alcohol from said alcohol-organic solvent phase;
   wherein said low-level alcohol-organic solvent extract phase from the fermentation liquor is such that the alcohol content in the remaining fermentation liquor is maintained sufficiently low so that it does not destroy the microorganisms in the fermentation liquor; and
   returning all material components of said aqueous raffinate comprising microorganisms and unextracted alcohol to said fermentation unit.

2. The method of claim 1, which further comprises conducting said fermentation by continuously admitting fermentable biomass feedstock and fermenting microorganisms into said fermentation unit and continuously withdrawing portions of fermentation liquor for extraction and sludge wastes from said unit.

3. The method of claim 1, which further comprises:
   adding absolute alcohol obtained from said separation step to said extraction step to facilitate drying of the alcohol in the solvent-alcohol extract phase.

4. The method of claim 1, which further comprises:
   separating said alcohol from said alcohol-solvent phase by vacuum distillation;
   condensing the absolute alcohol distillate; and
   returning the solvent phase to said extraction step.

5. The method of claim 1, wherein said biomass feedstock is molasses, sugar cane or sugar beets or a grain selected from the group consisting of corn, barley and wheat.

6. The method of claim 1, wherein said fermentation is conducted at a temperature from 25° to 35° C.

7. The method of claim 1, wherein said fermentation is conducted at a temperature as high as 75° C. to 95° C.

8. The method of claim 1, wherein said solvent system contains an extractant which is capable of hydrogen bonding with water or alcohol.

9. The method of claim 8, wherein said extractant is an alkyl or aromatic alcohol, an ether or a carboxylic acid.

10. the method of claim 9, wherein said alcohol extractant is a high boiling alcohol having an alkyl group of at least ten carbon atoms, said high boiling alcohol not being combined with a hydrophobic solvent.

11. The method of claim 9, wherein said extractant is a solvent selected from the group consisting of isodecanol, 2-ethylhexanol, 2-methyl-2-pentanol, 4-heptanol, 3-ethyl-3-pentanol and mixtures thereof.

12. The method of claim 1, wherein the solvent component of said organic solvent system is a hydrocarbon material selected from the group consisting of dodecane, kerosene, gasoline and diisopropylbenzene.

13. The method of claim 1, wherein the extractant of said solvent system is a solvent selected from the group consisting of a symmetric or unsymmetric alkyl or aryl phosphate, phosphonate, phosphine oxide, sulfoxide, sulfone and an amine oxide or a quarternary ammonium or phosphonium salt of a sterically hindered carboxylic acid.

14. The method of claim 1, wherein the alcohol product of fermentation is ethanol or butanol.

* * * * *